United States Patent
Fu et al.

(10) Patent No.: US 11,884,644 B1
(45) Date of Patent: Jan. 30, 2024

(54) METHOD FOR SYNTHESIZING (S)-NICOTINE AND INTERMEDIATE THEREOF

(71) Applicant: Shandong Jincheng Pharmaceutical Chemical Co., Ltd., Zibo (CN)

(72) Inventors: Kai Fu, Zibo (CN); Jiaquan Li, Zibo (CN); Peng Wang, Zibo (CN); Qinyuan Ma, Zibo (CN); Xicheng Zhang, Zibo (CN); Gengxiu Zheng, Zibo (CN); Ruihua Hu, Zibo (CN)

(73) Assignee: Shandong Jincheng Pharmaceutical Chemical Co., Ltd., Zibo (CN)

( * ) Notice: Subject to any disclaimer, the term of this patent is extended or adjusted under 35 U.S.C. 154(b) by 0 days.

(21) Appl. No.: 18/460,072

(22) Filed: Sep. 1, 2023

(30) Foreign Application Priority Data

Feb. 20, 2023 (CN) .......................... 202310133879.6

(51) Int. Cl.
*C07D 401/04* (2006.01)
*C12P 17/12* (2006.01)
*C07D 213/38* (2006.01)

(52) U.S. Cl.
CPC ......... *C07D 401/04* (2013.01); *C07D 213/38* (2013.01); *C12P 17/12* (2013.01); *C07B 2200/07* (2013.01)

(58) Field of Classification Search
CPC ...... C07D 401/04; C07D 213/38; C12P 17/12
USPC ...................................................... 546/250
See application file for complete search history.

(56) References Cited

FOREIGN PATENT DOCUMENTS

| CN | 110551771 A | 12/2019 |
|---|---|---|
| CN | 113373188 A | 9/2021 |
| CN | 115404249 A | 11/2022 |
| WO | 2014174505 A2 | 10/2014 |
| WO | 2020098978 A1 | 5/2020 |

OTHER PUBLICATIONS

First Office Action dated Mar. 24, 2023, by the China National Intellectual Property Administration in corresponding Chinese Patent Application No. 202310133879.6, and an English translation of the Office Action. (20 pages).

Notification of Granting Patent Right of Invention dated Apr. 11, 2023, by the China National Intellectual Property Administration in corresponding Chinese Patent Application No. 202310133879.6, and an English translation of the Notification. (6 pages).

*Primary Examiner* — Kahsay Habte
(74) *Attorney, Agent, or Firm* — BUCHANAN, INGERSOLL & ROONEY PC

(57) ABSTRACT

Disclosed is a method for synthesizing (S)-nicotine and an intermediate thereof, which belongs to the field of synthesizing a heterocyclic compound. A chiral amino group is introduced into 4-hydroxy-1-(3-pyridyl)-1-butanone by transaminase chiral catalysis in the presence of an amino donor to obtain (S)-4-amino-4-(3-pyridyl)-1-butanol. An N-methylation reaction is performed on (S)-4-amino-4-(3-pyridyl)-1-butanol with a methylating agent to obtain (S)-4-(methylamino)-4-(3-pyridyl)-1-butanol. The intermediate is reacted with an acylating agent or a halogenating agent to convert an alcoholic hydroxyl group into a sulfonate group or a halogen. Finally, a ring closure reaction is performed to obtain (S)-nicotine in an alkaline condition. The raw materials are cheap and readily available, the reaction conditions are mild, the operation is simple, and the cost is low. A single configuration of (S)-nicotine can be obtained with high selectivity, and thus the method is particularly suitable for industrial production of (S)-nicotine.

20 Claims, 6 Drawing Sheets

METHOD FOR SYNTHESIZING (S)-NICOTINE AND INTERMEDIATE THEREOF

FIELD OF THE INVENTION

The present disclosure relates to the field of synthesizing a heterocyclic compound, and in particular, to a method for synthesizing (S)-nicotine and an intermediate thereof.

BACKGROUND OF THE INVENTION

Nicotine, also referred to as alkaloid of tobacco, is the main alkaloid in tobacco. Nicotine has strong physiological activity in tobacco leaves. Generally, a nicotine content in tobacco leaves is 1-3%, and a nicotine content in special tobacco leaves may reach 10-14%. When a nicotine content in tobacco leaves is >1%, the tobacco leaves are worth extracting. There are two commercial products of nicotine. One is nicotine sulfate 40% with a nicotine content of ≥40%, and the other is referred to as pure nicotine with a nicotine content of >95%. Nicotine is mainly used in producing electronic cigarettes, smoking cessation medications, pesticides, cigarette additives, and the like.

In recent years, with the growth of fine chemical industry, pharmacy, organic synthesis, national defense, agriculture, and tobacco industry, nicotine is increasingly used. In addition, the demand for nicotine in China and other countries is growing. Thus, nicotine has a broad prospect of growth.

Chemical synthesis of nicotine has been reported. Patent No. WO2020098978A1 discloses a method for preparing (S)-nicotine from myosamine. The method includes: reducing myosamine with an enzyme having imine reduction activity to obtain an intermediate nomicotine having high optical purity, and performing a Mannich reaction using formaldehyde and formic acid to obtain (S)-nicotine. The process of the chemical reaction is as follows:

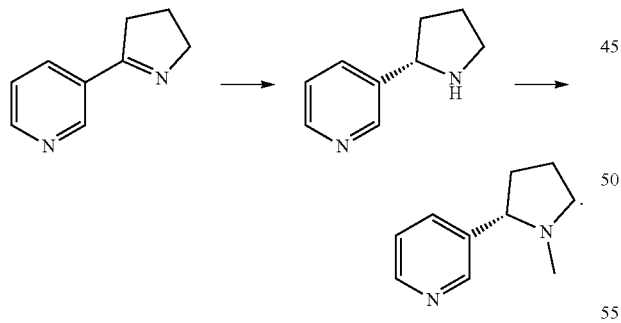

In the above patent, myosamine is prepared by nicotinate and vinylpyrrolidone as raw materials. Unfortunately, vinylpyrrolidone is expensive and has a high production cost.

Patent No. WO2014174505A2 discloses a method for preparing optically active nicotine. The method includes: reducing 4-(methylamino)-1-pyridyl-3-ylbutan-1-ketone with a carbonyl reductase, and performing an alkaline ring closure reaction to obtain (S)-nicotine. The process of the chemical reaction is as follows:

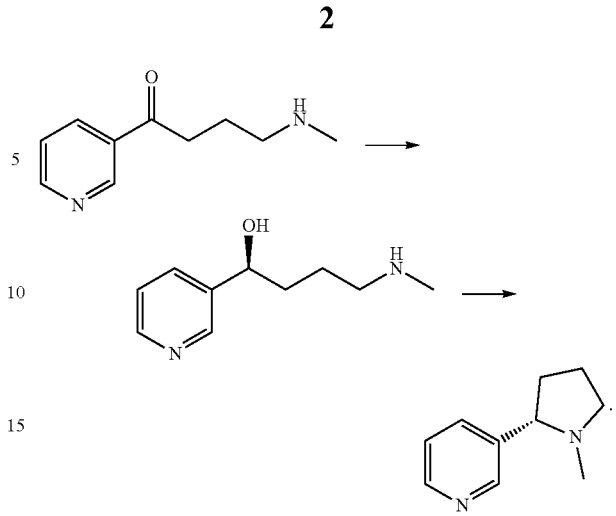

The process could not be put into large-scale production because the raw materials thereof are not readily available. Besides, the yield of the product is low for harsh reaction conditions.

SUMMARY OF THE INVENTION

To solve the problems of high cost and low yield in chemical synthesis of nicotine, the present disclosure provides a method for synthesizing (S)-nicotine and an intermediate thereof.

To achieve the above objective, the technical solutions adopted in the present disclosure are described below.

The present disclosure provides a method for preparing a chiral intermediate (S)-4-amino-4-(3-pyridyl)-1-butanol (Formula II) for preparing (S)-nicotine, including:
performing a transamination reaction between 4-hydroxy-1-(3-pyridyl)-1-butanone and an amino donor to generate (S)-4-amino-4-(3-pyridyl)-1-butanol in catalysis of transaminase and coenzyme pyridoxal phosphate, the transaminase being one of transaminases with NCBI accession numbers being XP_007730450, 5FR9_A, WP_040602310 and XP_748821 or a homologue thereof.

The intermediate (S)-4-amino-4-(3-pyridyl)-1-butanol has the following structural formula:

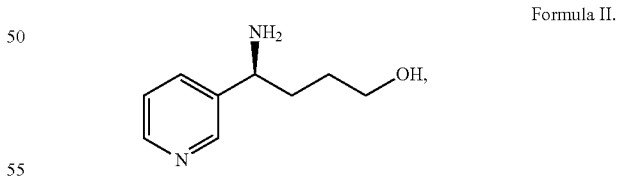

Formula II.

Preferably, a temperature of the transamination reaction is 20-32° C., pH of the reaction is 6.5-8.0, and time for the reaction is 6-24 h. Further preferably, the temperature of the transamination reaction is 28-30° C., the pH of the reaction is 7.0-8.0, and the time for the reaction is 8-12 h.

Preferably, a mass ratio of 4-hydroxy-1-(3-pyridyl)-1-butanone and the transaminase is 1: 1-7, and is further preferably 1: 3-7. The coenzyme pyridoxal phosphate (PLP) is an auxiliary material required for the transaminase catalytic reaction, and those skilled in the art may select the amount according to needs. In the present disclosure, the transaminase is added into the reaction system in the form of an enzyme solution, and a content of the transaminase in the enzyme solution is 15-20%.

Preferably, in the above transamination reaction, 4-hydroxy-1-(3-pyridyl)-1-butanone is dissolved in a potassium dihydrogen phosphate buffer to prepare a solution, and then the solution is added into the transamination reaction system with a concentration of 4-hydroxy-1-(3-pyridyl)-1-butanone ranging from 1-12 g/L. Preferably, the concentration ranges from 4-6 g/L.

Preferably, a molar ratio of 4-hydroxy-1-(3-pyridyl)-1-butanone and the amino donor is 1: 1-20, and is further preferably 1: 9-10. The amino donor is one or more of isopropylamine, n-propylamine, alanine and a-phenylethylamine, and is preferably the isopropylamine.

The present disclosure further provides a method for synthesizing a chiral intermediate (S)-4-(methylamino)-4-(3-pyridyl)-1-butanol for preparing (S)-nicotine, including:
  performing a transamination reaction between 4-hydroxy-1-(3-pyridyl)-1-butanone and an amino donor to generate (S)-4-amino-4-(3-pyridyl)-1-butanol in catalysis of transaminase and coenzyme pyridoxal phosphate, the transaminase being one of transaminases with NCBI accession numbers being XP_007730450, 5FR9_A, WP_040602310 and XP_748821 or a homologue thereof; and
  performing an N-methylation reaction on (S)-4-amino-4-(3-pyridyl)-1-butanol with a methylating agent to obtain (S)-4-(methylamino)-4-(3-pyridyl)-1-butanol having the following structural formula:

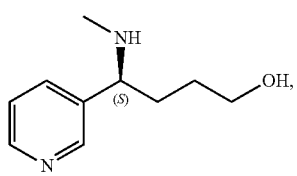

Formula III.

Preferably, the methylating agent is one or more of dimethyl sulfate, methyl iodide or a combination of formic acid and formaldehyde, and is preferably the dimethyl sulfate.

Preferably, a molar ratio of (S)-4-amino-4-(3-pyridyl)-1-butanol and the methylating agent is 1: 1.05-1.3. Further preferably, the molar ratio of (S)-4-amino-4-(3-pyridyl)-1-butanol and the methylating agent is 1: 1.05-1.1.

Preferably, a temperature of the methylation reaction is 0-10° C. Further preferably, the temperature of the reaction is 5-10° C.

Preferably, time for the reaction is 4-8 h. Further preferably, the time for the reaction is 4-6 h.

The present disclosure further provides a method for synthesizing (S)-nicotine, including:
  making a chiral intermediate (S)-4-(methylamino)-4-(3-pyridyl)-1-butanol react with an acylating agent or a halogenating agent to convert an alcoholic hydroxyl group thereof into a sulfonate group or a halogen; and directly performing a ring closure reaction on a product without separation to obtain a final product (S)-nicotine with the reaction controlled in an alkaline condition.

Preferably, the acylating agent is one or more of methanesulfonyl chloride, benzenesulfonyl chloride and p-toluenesulfonyl chloride, and is preferably the methanesulfonyl chloride or the p-toluenesulfonyl chloride; the halogenating agent is one or more of hydrobromic acid and thionyl chloride.

Preferably, a molar ratio of (S)-4-(methylamino)-4-(3-pyridyl)-1-butanol and the acylating agent or the halogenating agent is 1: 1.0-2.0, and the preferred molar ratio is 1: 1.0-1.1. A temperature of the reaction is −5-25° C., and time is 1-3 h. Preferably, the temperature is 20-25° C., and the time is 1.5-2 h.

The acylation reaction or halogenation reaction often require alkali to catalyze. Preferably, the alkali includes, but is not limited to, triethylamine, N-methylmorpholine, N,N-diisopropylethyl amine, pyridine and 1,8-Diazabicyclo (5.4.0)undec-7-ene (DBU), and is preferably the triethylamine or the N,N-diisopropylethyl amine. A molar ratio of the triethylamine or the N,N-diisopropylethyl amine and (S)-4-(methylamino)-4-(3-pyridyl)-1-butanol is 1-2: 1.

The method of the present disclosure does not need to purify the acylation or halogenation product, and the obtained reaction solution may be directly heated in an alkaline condition (pH>8) to achieve the ring closure reaction and obtain the target product (S)-nicotine. If pH<8, it is necessary to add an appropriate amount of alkali to adjust the pH to be greater than 8.

Preferably, a temperature of the ring closure reaction is 20-50° C. Further preferably, the temperature of the reaction is 40-50° C., and time for the reaction is 2-3 h.

Compared with the related art, the present disclosure has the following advantages.

1. In the present disclosure, the intermediate of (S)-nicotine is obtained by the transamination reaction with a biological transaminase and the N-methylation reaction, and then the intermediate is further reacted to obtain (S)-nicotine. The method greatly reduces the cost compared with the preparation of (S)-nicotine using an expensive metal catalyst reported. The agents used are commonly used cheap agents, and the yield is also increased, greatly reducing the production cost.
2. The reactions of the present disclosure are in relatively mild conditions, and the next reaction can be directly performed for each reaction without separation. Therefore, the operation is simple, and the raw materials are widely available, easily achieving the industrial production.
3. The prepared (S)-nicotine according to the present disclosure has high optical purity of more than 99.5% and is free of other harmful tobacco compounds. Thus, it can be directly used in further product development.

DETAILED DESCRIPTION OF THE EMBODIMENTS

Figure 1:
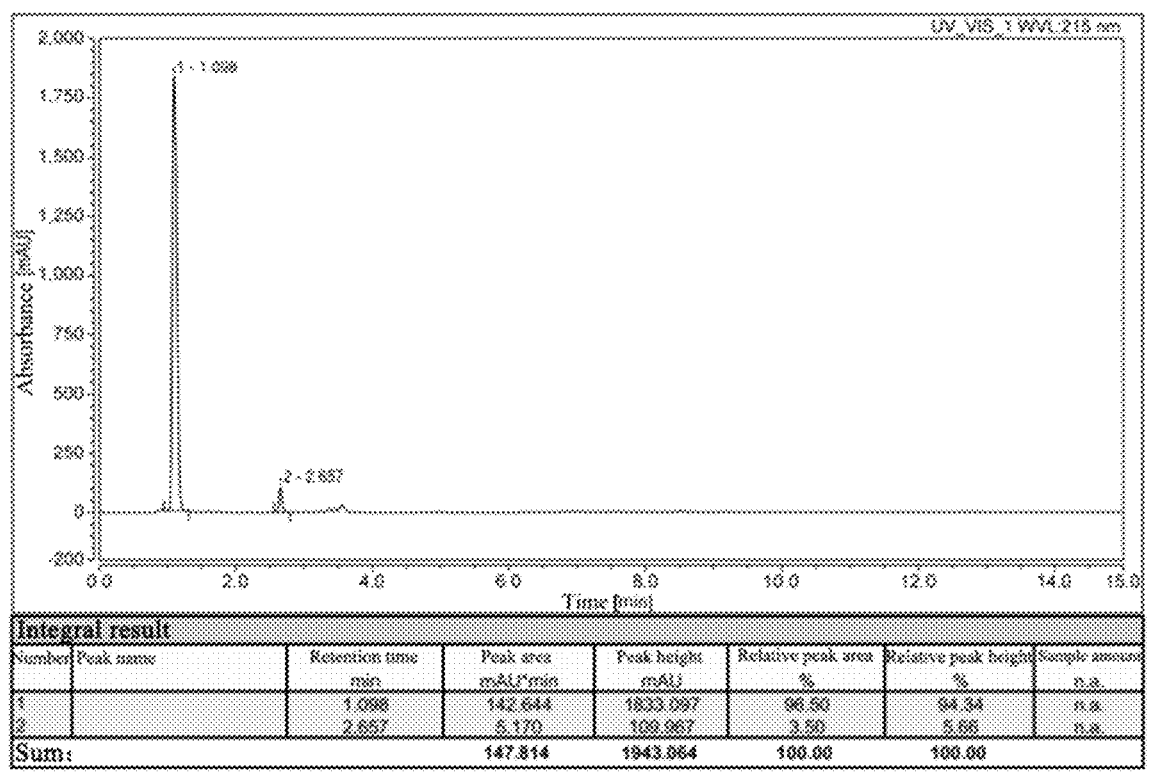
FIG. 1 is a liquid chromatogram of the obtained product 4-amino-4-(3-pyridyl)-1-butanol in step (1) of example 1.

In conjunction with the embodiments, it is apparent that the embodiments described below are only some, but not all embodiments of the present disclosure. Based on the embodiments of the present disclosure, all other embodiments obtained by those skilled in the art without creative effort are within the scope of the present disclosure. The PLP used in the embodiments of the present disclosure was purchased from Maclean Biochemical Technology Co., Ltd.

The transaminases A-D used in the implementations of the present disclosure were obtained by gene mining, screening from the NCBI database to obtain target genes of transaminases, linking to the expression vector pET-28a, transforming into an expression host *E. coli*, and inducing protein expression. *E. coli* was introduced into a fermentation medium for expansion and centrifugated to obtain a resting cell. The resting cell was suspended in an aqueous buffer solution, and the cell wall was broken by a high-pressure homogenizer to obtain a transaminase solution. The transaminase content % in the transaminase solution=the weight of the resting cell/the weight of the buffer solution× 100%.

The raw material 4-hydroxy-1-(3-pyridyl)-1-butanone used in the embodiments of the present disclosure may be synthesized by the methods known in the related art. The present disclosure is preferably synthesized by the following method. A condensation reaction was performed between nicotinate and γ-butyrolactone under alkaline catalysis, and a condensation product was hydrolyzed in an acidic condition to obtain 4-hydroxy-1-(3-pyridyl)-1-butanone. Reference may be made to the method described in the patent No. CN115627282A (202211621603.4).

The sources of the transaminases in the present disclosure are shown in Table 1:

TABLE 1

| Enzyme type | NCBI accession number | Source |
|---|---|---|
| A | XP_007730450 | *Caproniaepimyces* CBS 606.96 |
| B | 5FR9_A | *Artlrobacter* sp. |
| C | WP_040602310 | *Paracoccus* |
| D | XP_748821 | *Aspergillus fumigatus* Af293 |

A method for synthesizing (S)-nicotine in the present disclosure includes the following steps.

(1) A chiral amino group was introduced into 4-hydroxy-1-(3-pyridyl)-1-butanone by transaminase chiral catalysis in the presence of an amino donor to obtain (S)-4-amino-4-(3-pyridyl)-1-butanol.

(2) An N-methylation reaction was performed on (S)-4-amino-4-(3-pyridyl)-1-butanol with a methylating agent to obtain (S)-4-(methylamino)-4-(3-pyridyl)-1-butanol.

(3) An alcoholic hydroxyl group of (S)-4-(methylamino)-4-(3-pyridyl)-1-butanol was converted into a sulfonate or a halogen using an acylating agent or a halogenating agent; and a ring closure reaction was directly performed on a product without separation to obtain a final product (S)-nicotine in an alkaline condition.

The process route is as follows:

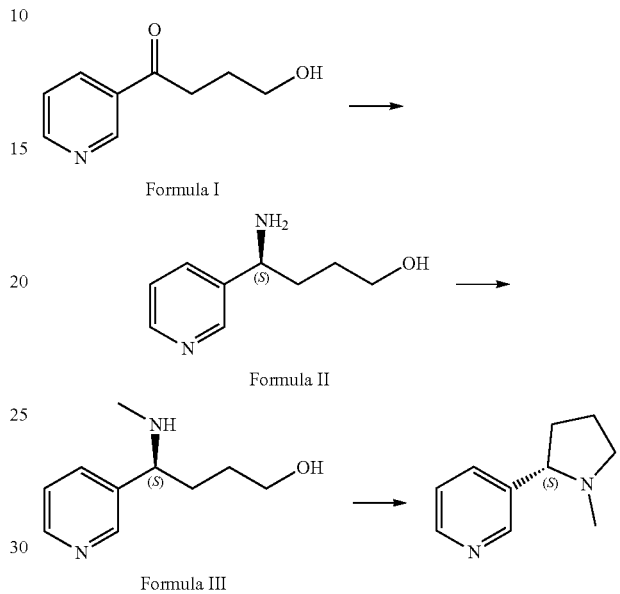

Example 1

Synthesizing (S)-4-(methylamino)-4-(3-pyridyl)-1-butanol includes the following specific steps.

(1) 18.0 g of 4-hydroxy-1-(3-pyridyl)-1-butanone (the substrate, compound of Formula I) (0.11 mol, 1.0 eq) was dissolved in 3000 ml of potassium dihydrogen phosphate buffer with a concentration of 0.2 M (the substrate concentration is 6 g/L); 0.08 g of PLP (0.33 mmol, 0.003 eq), 64.4 g of isopropylamine (1.09 mol, 10.0 eq), and an enzyme solution (the addition amount of the enzyme solution and the transaminase content are shown in Table 2, and the amounts of transaminases with different activities are about 5 times the mass of the substrate 4-hydroxy-1-(3-pyridyl)-1-butanone, i.e., enzyme: substrate=5) were added for the transamination reaction. The pH=7 was adjusted using 3.5% hydrochloric acid, the reaction temperature was 28-30° C., and the reaction time was 12 h.

After completion of the reaction as determined by HPLC, celite (300 g) was added to help filter, stirred for 20 min, and filtered. The filtrate was extracted three times with 300 ml×3 dichloromethane, and the organic phase was dried using $Na_2SO_4$ to obtain a dichloromethane solution of (S)-4-amino-4-(3-pyridyl)-1-butanol (compound of Formula II). The solvent was distilled off to obtain (S)-4-amino-4-(3-pyridyl)-1-butanol.

The experimental results for different transaminases are described in detail in Table 2. The yield of (S)-4-amino-4-(3-pyridyl)-1-butanol was calculated based on the weight of (S)-4-amino-4-(3-pyridyl)-1-butanol obtained after evaporation of the solvent dichloromethane.

TABLE 2

| Serial number | Enzyme solution [g] | Enzyme type | Transaminase content [%] | Conversion rate of compound of Formula I [%] | Optical purity of compound of Formula II [%] | Yield of compound of Formula II [%] |
|---|---|---|---|---|---|---|
| 1-1 | 563 | A | 16.0 | 96.5 | 99.8 | 91 |
| 1-2 | 511 | B | 17.6 | 95.1 | 97.1 | 86 |
| 1-3 | 552 | C | 16.3 | 95.6 | 96.7 | 83 |
| 1-4 | 500 | D | 18.0 | 94.3 | 95.5 | 80 |

Figure 2:
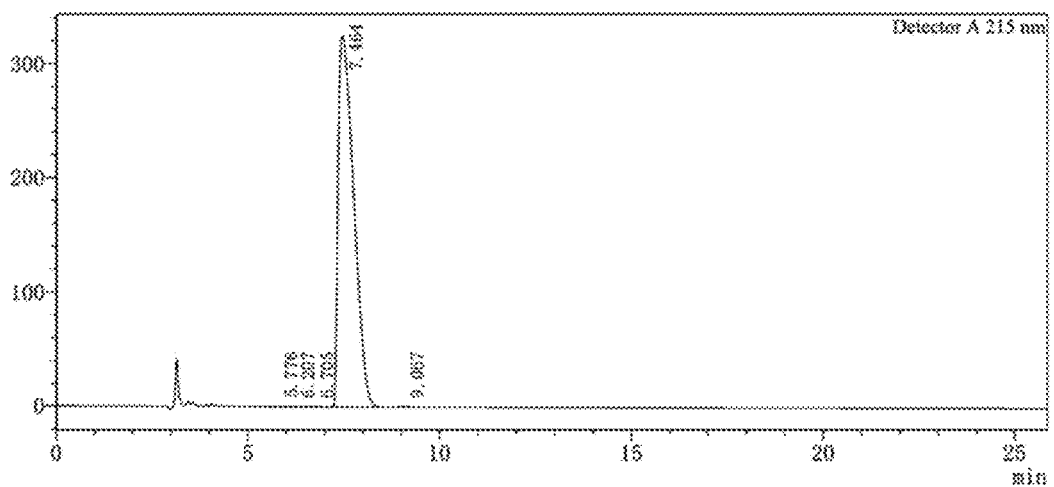
FIG. 2 is a spectrogram showing optical purity of the obtained product 4-amino-4-(3-pyridyl)-1-butanol in step (1) of example 1.
Figure 3:
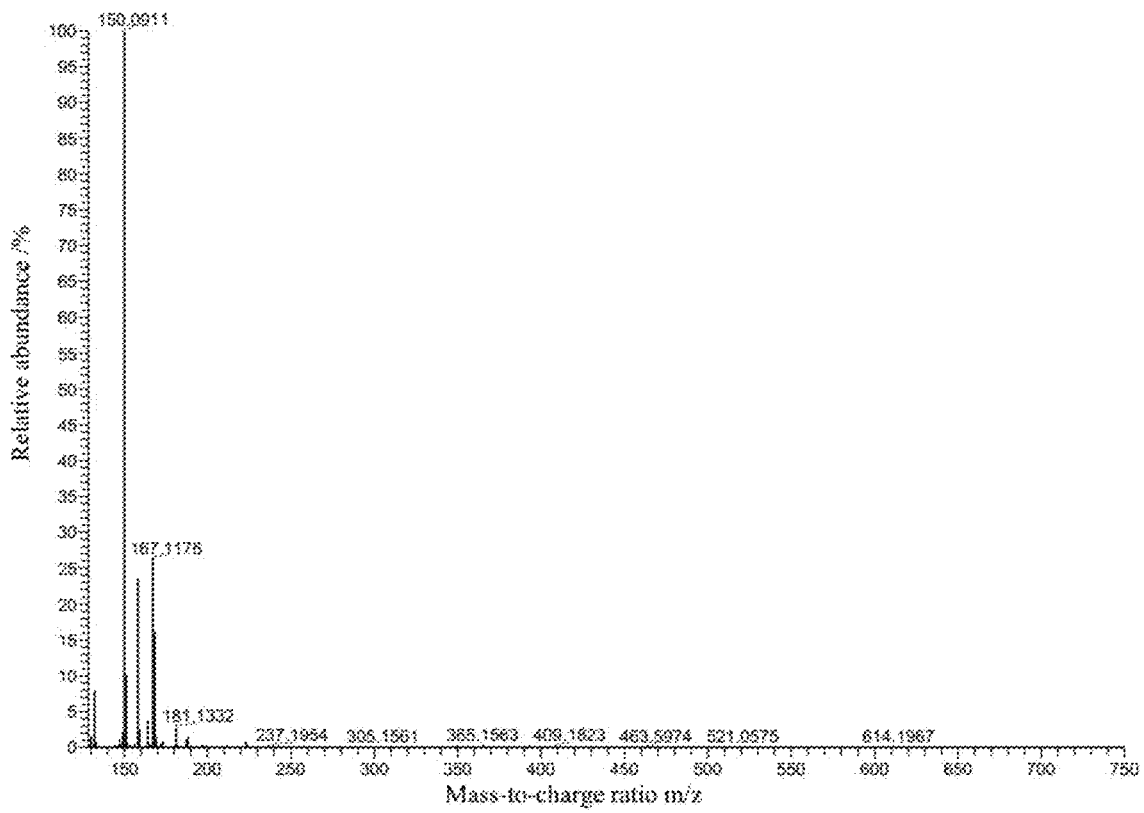
FIG. 3 is a mass spectrogram of the obtained product 4-amino-4-(3-pyridyl)-1-butanol in step (1) of example 1.
Figure 4:
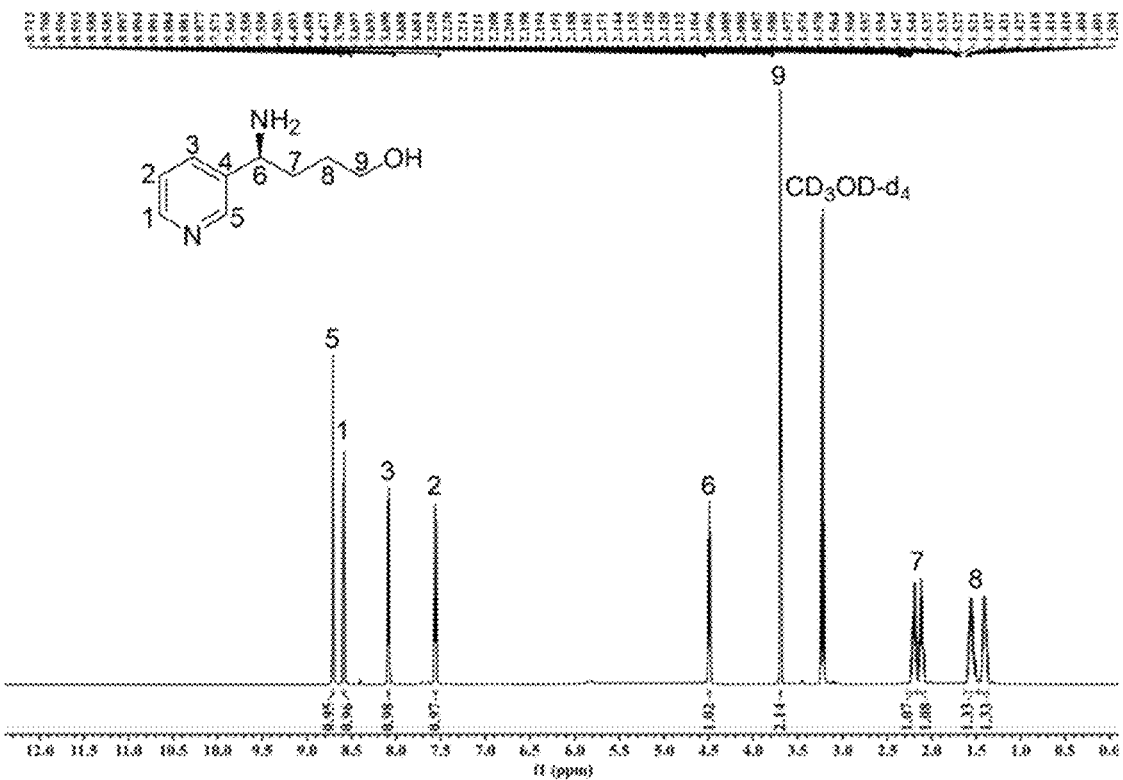
FIG. 4 is a H-NMR spectrogram of the obtained product 4-amino-4-(3-pyridyl)-1-butanol in step (1) of example 1.
Figure 5:
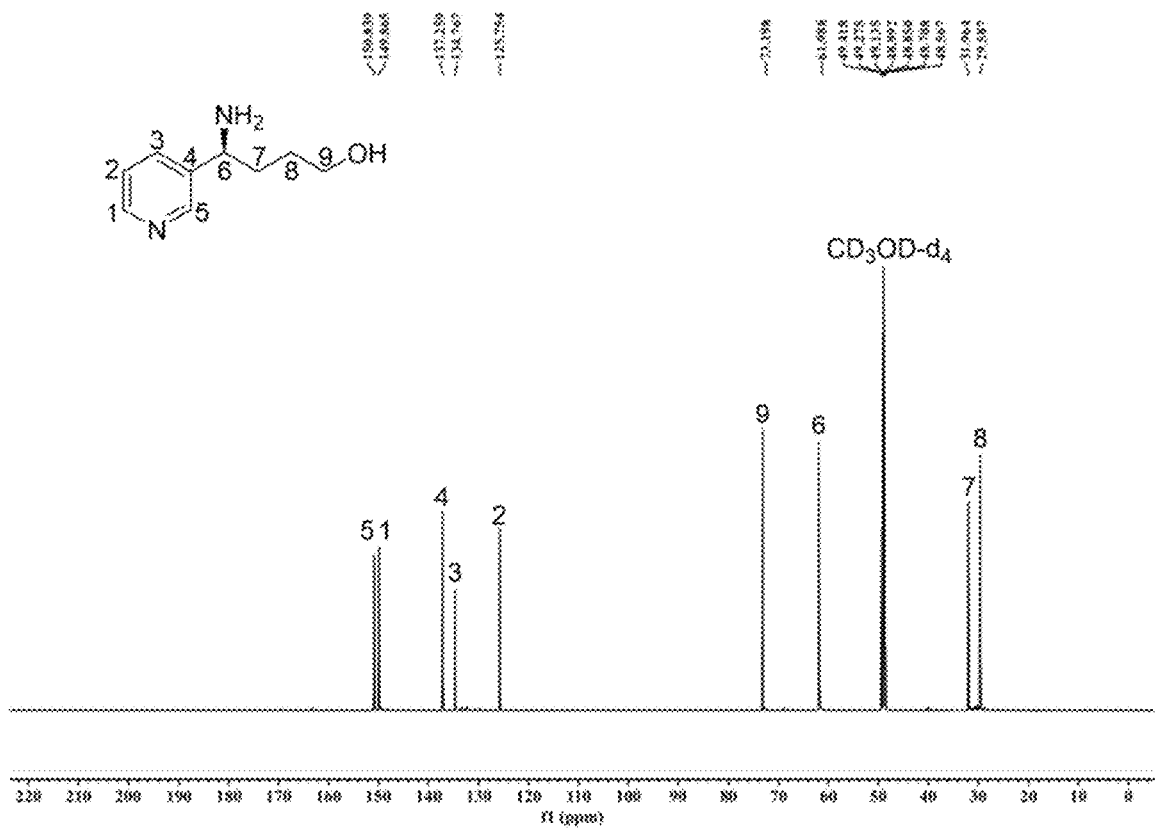
FIG. 5 is a C-NMR spectrogram of the obtained product 4-amino-4-(3-pyridyl)-1-butanol in step (1) of example 1.

In Table 2, the conversion rate of the compound of Formula I is calculated as: conversion rate %=(mass of I before reaction—mass of I remaining after reaction)/mass of I before reaction×100%. FIG. 1 is a liquid purity spectrogram of the compound of Formula II in experiment 1-1 with a retention time of 1.098 min for (S)-4-amino-4-(3-pyridyl)-1-butanol. FIG. 2 is a spectrogram showing optical purity of the compound of Formula II in experiment 1-1 with retention time being 7.464 min. FIG. 3 is a HRMS spectrogram of the compound of Formula II in experiment 1-1 with (ESI, m/z): $[M^+H]^+$=167.1176, and theoretical m/z=167.1179. FIG. 4 is a H-NMR spectrogram of the compound of Formula II in experiment 1-1 with $^1$HNMR (600 MHz, Methanol-d4) δ8.69 (d, 1H), 8.60 (dd, 1H), 8.06 (dt, 1H), 7.57 (dd, 1H), 4.47 (dd, 1H), 3.70 (t, 2H), 2.16 (m, 2H), and 1.51 (m, 2H). FIG. 5 is a C-NMR spectrogram of the compound of Formula II in experiment 1-1with $^{13}$CNMR (151 MHz, Methanol-d4) δ150.84, 149.87, 137.26, 134.77, 125.76, 73.20, 61.99, 31.96, and 29.59.

HPLC conditions for determining the chemical purity of the compound of Formula II: An X-Bridge C18 column was used, an eluent contained a mixture of (i) 9 mM ammonium phosphate water/acetonitrile solution (water/acetonitrile=9: 1) and (ii) acetonitrile, and a gradient program was as follows. With an initial ratio of 100: 0, at 0-6 min, the ratio was 22: 78; at 6-11 min, the ratio was 22: 78; at 11-12 min, the ratio was 100: 0; at 12-15 minutes, the ratio was 100: 0. A flow rate was 1.0 ml/min, and a column temperature was 30° C. The conditions of the detector were UV absorption at a wavelength of 215 nm.

HPLC conditions for determining the optical purity of the compound of Formula II: A Chiralpak AS-H column was used, an eluent with a ratio of n-hexane: ethanol=80: 20 was used for elution, a flow rate was 1.0 ml/min, and a column temperature was 30° C. The conditions of the detector were UV absorption at a wavelength of 215 nm.

(2) A dichloromethane solution of (S)-4-amino-4-(3-pyridyl)-1-butanol (containing 16.5 g of (S)-4-amino-4-(3-pyridyl)-1-butanol (0.10 mol, 1.0 eq)) prepared in experiment 1-1 in step (1) was taken and cooled to 5° C.; and 13.8 g of dimethyl sulfate (0.11 mol, 1.1 eq) and 26.5 g of sodium hydroxide solution (containing NaOH 0.20 mol, 2.0 eq) at a concentration of 30% were added dropwise. After the addition dropwise, the temperature was controlled at 5-10° C. for 4 h. After the completion of the reaction, the layers were separated, and the organic phase was dried using $Na_2SO_4$ to obtain a dichloromethane solution of (S)-4-(methylamino)-4-(3-pyridyl)-1-butanol (the compound of Formula III). The solvent was distilled off to obtain 16.5 g of (S)-4-(methylamino)-4-(3-pyridyl)-1-butanol with a yield of 92.2%.

Figure 6:
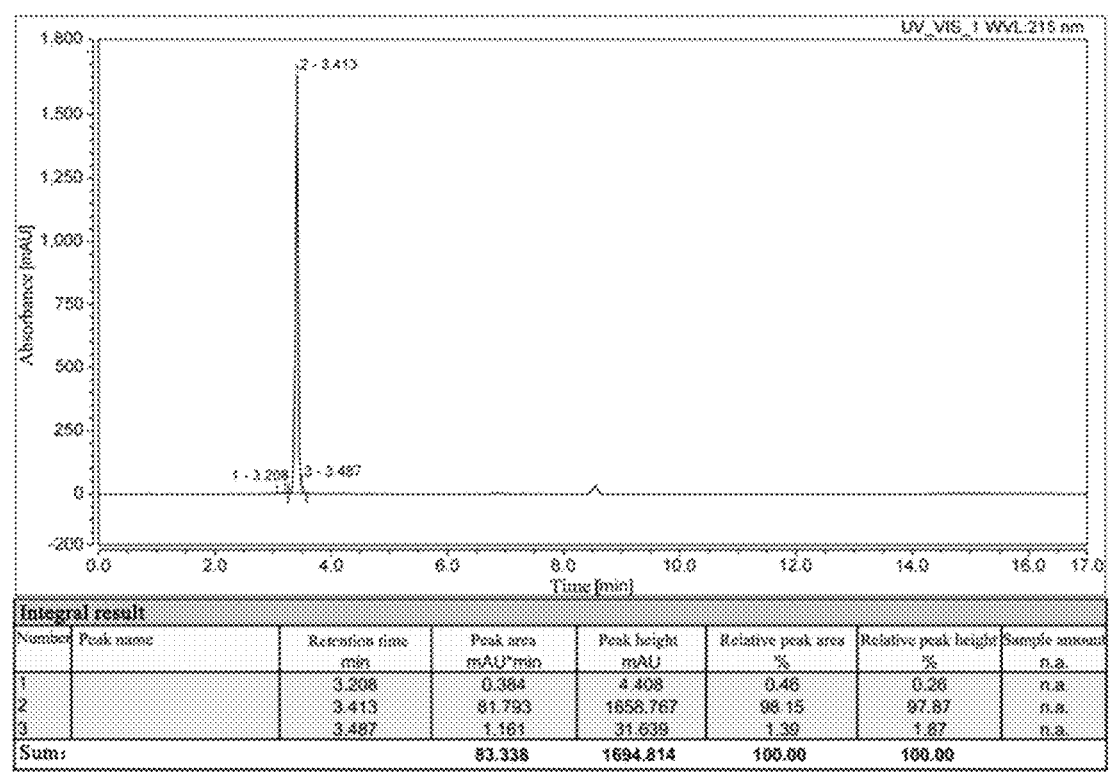
FIG. 6 is a liquid chromatogram of the obtained product (S)-4-(methylamino)-4-(3-pyridyl)-1-butanol in step (2) of example 1.
Figure 7:
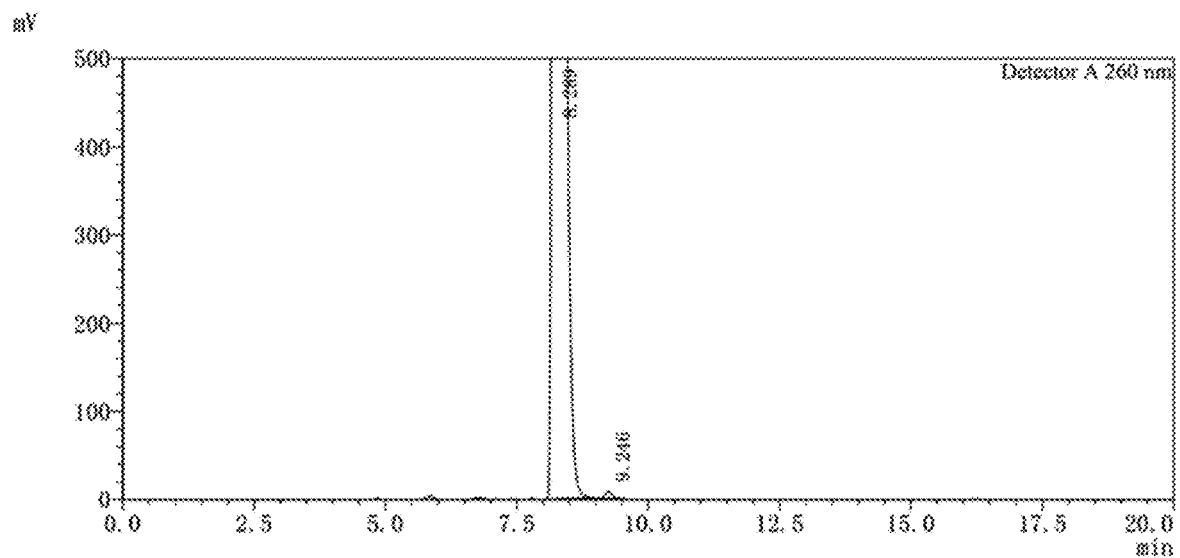
FIG. 7 is a spectrogram showing optical purity of the obtained product (S)-4-(methylamino)-4-(3-pyridyl)-1-butanol in step (2) of example 1.
Figure 8:
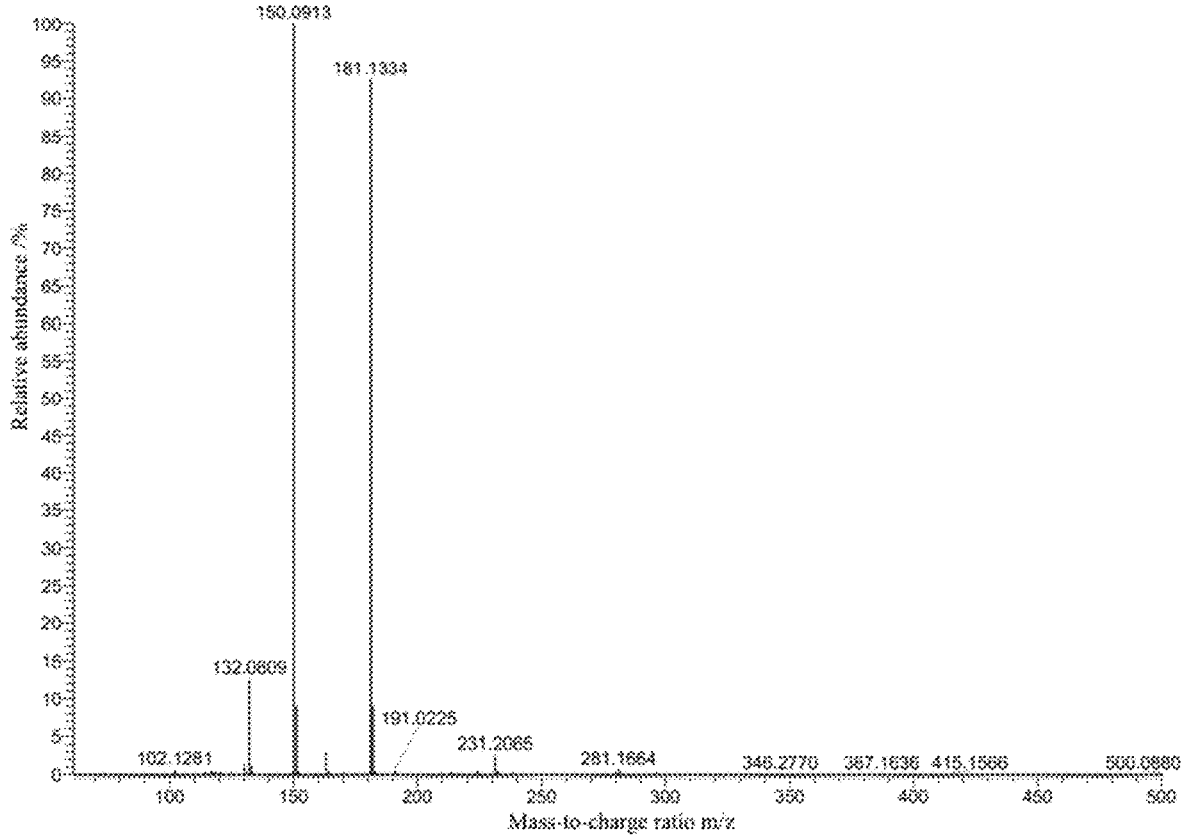
FIG. 8 is a mass spectrogram of the obtained product (S)-4-(methylamino)-4-(3-pyridyl)-1-butanol in step (2) of example 1.

FIG. 6 is a liquid phase purity spectrogram of the compound of Formula III obtained in step (2) with retention time of the compound of Formula III being 3.413 min. FIG. 7 is a spectrogram showing optical purity of the compound of Formula III obtained in step (2) with retention time of the compound of Formula III being 8.289 min. FIG. 8 is a HRMS spectrogram of the compound of Formula III obtained in step (2) with (ESI, m/z): $[M^+H]^+$=181.1334, and theoretical m/z=181.1335.

Example 2

This example demonstrates the effects of transaminases provided in the present disclosure on the conversion rate of different amino donors and the optical purity of the obtained chiral product (S)-4-amino-4-(3-pyridyl)-1-butanol. The reaction conditions were the same as 1-1 in example 1, except that the amino donor was different.

The reaction of step (1) was performed, the amino donor used and the results are described in detail in Table 3.

TABLE 3

| Serial number | Amino donor | Conversion rate of compound of Formula I [%] | Optical purity of compound of Formula II [%] |
|---|---|---|---|
| 2-1 | N-propylamine | 94.3 | 99.8 |
| 2-2 | α-phenylethylamine | 92.5 | 99.1 |
| 2-3 | Alanine | 90.6 | 99.2 |

Example 3

This example demonstrates the effects of transaminases provided in the present disclosure on the conversion rate of different substrate concentrations and the optical purity of the obtained chiral product (S)-4-amino-4-(3-pyridyl)-1-butanol. The reaction conditions were the same as experiment 1-1 in example 1, except that the concentration of the substrate 4-hydroxy-1-(3-pyridyl)-1-butanone was different. The substrate concentrations and results are shown in Table 4.

TABLE 4

| Serial number | Substrate concentration [g/L] | Conversion rate of compound of Formula I [%] | Optical purity of compound of Formula II [%] |
|---|---|---|---|
| 3-1 | 1 | 94.2 | 99.7 |
| 3-2 | 3 | 95.8 | 99.8 |
| 3-3 | 9 | 92.9 | 98.7 |
| 3-4 | 12 | 86.8 | 98.0 |

Example 4

This example demonstrates the effects of the amount of the transaminase solution on the conversion rate of the compound of Formula I and the optical purity of the obtained chiral product (S)-4-amino-4-(3-pyridyl)-1-butanol. The reaction was performed by the same method as in experiment 1-1 in example 1, except that in step (1), the feed weight ratio of transaminase A and substrate 4-hydroxy-1-(3-pyridyl)-1-butanone was different.

In this example, the amount of the substrate (S)-4-amino-4-(3-pyridyl)-1-butanol was 2 g, and the substrate concentration was 6 g/L as in example 1. The reaction of step (1) was performed using the transaminase A with different feed weight ratios (enzyme content of 16.0%, equivalent to the amount of pure enzyme=mass of enzyme solution x enzyme content). The feed weight of the enzyme and the results are described in detail in Table 5. The ratios of other raw materials and the substrate were the same as in example 1, and the actual addition amount was adjusted accordingly.

TABLE 5

| Serial number | Feed weight ratio (enzyme:substrate) | Amount of pure enzyme [g] | Conversion rate of compound of Formula I [%] | Optical purity of compound of Formula II [%] |
|---|---|---|---|---|
| 4-1 | 1.0 | 2 | 82.4 | 99.0 |
| 4-2 | 3.0 | 6 | 93.9 | 99.4 |
| 4-3 | 7.0 | 14 | 96.4 | 99.7 |

Example 5

Figure 9:
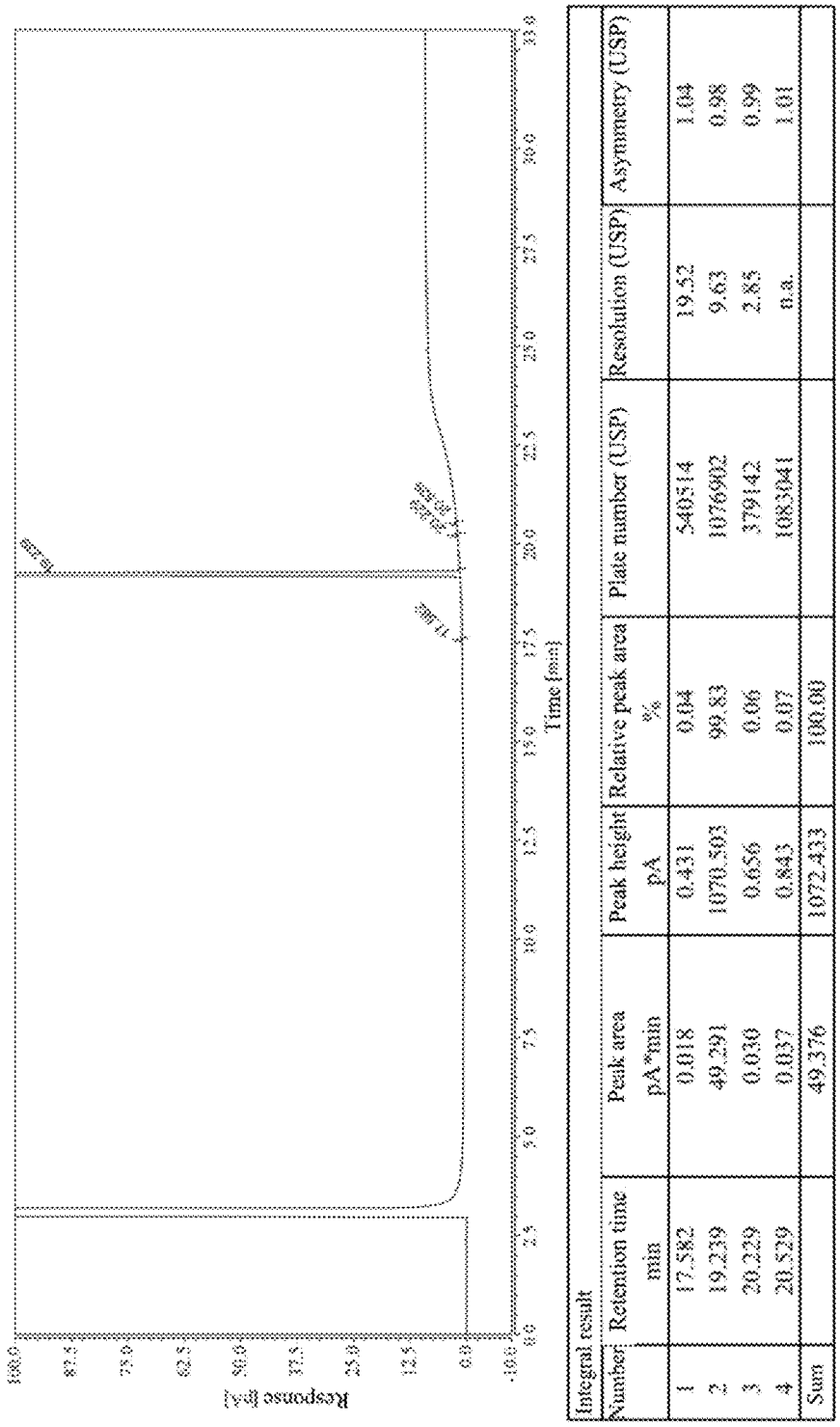
FIG. 9 is a spectrogram showing chemical purity of the obtained product (S)-nicotine in example 5.
Figure 10:
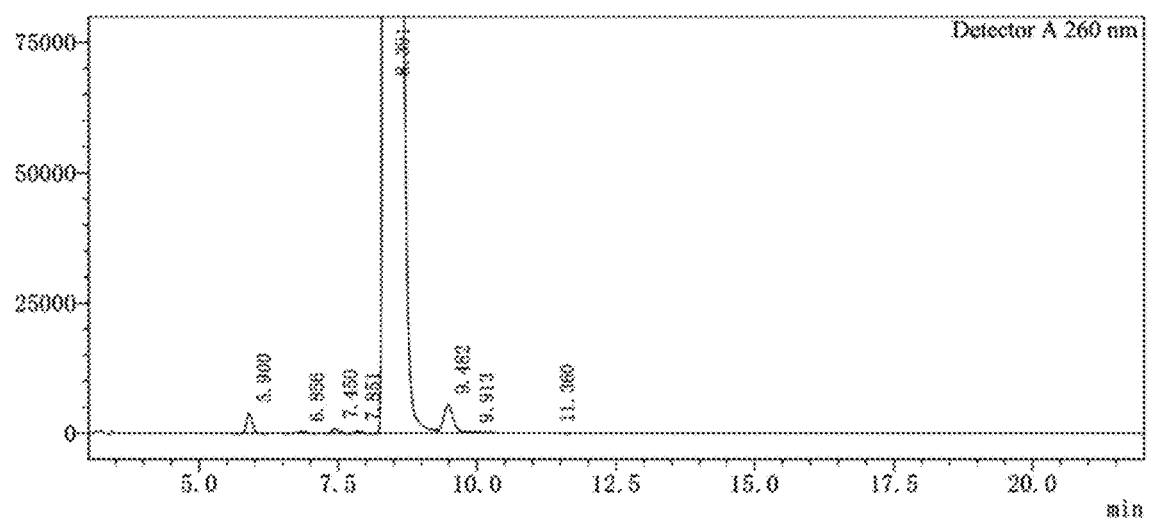
FIG. 10 is a spectrogram showing optical purity of the obtained product (S)-nicotine in example 5.

Synthesizing optically pure (S)-nicotine: the net weight of 16.5 g of the dichloromethane solution of (S)-4-(methylamino)-4-(3-pyridyl)-1-butanol (0.09 mol, 1.0 eq) prepared in experiment 1-1 in example 1 was taken, and 13.9 g of triethylamine (0.14 mol, 1.5 eq) was added. The temperature was cooled to 0° C., and 11.5 g of methanesulfonyl chloride (0.10 mol, 1.1 eq) was slowly added dropwise. After the addition dropwise, the temperature was raised to 20° C. and maintained for 2 h. After<1% of the HPLC central control raw materials was remained, the pH of the system was detected. If the pH<8, triethylamine was used to adjust pH>8, and the reaction solution was then warmed to 40° C. for 3 h. After the completion of the central control ring closure reaction, the reaction solution was washed with 300 ml of water, the aqueous phase was extracted once more with 300 ml of dichloromethane, and the organic phases were combined. $Na_2SO_4$ was added for drying, and the solvent was removed by concentration under reduced pressure to obtain crude (S)-nicotine. After further purification by distillation, 13.0 g of pure (S)-nicotine was obtained with a yield of 87.8% (total yield of 73.7% based on 4-hydroxy-1-(3-pyridyl)-1-butanone), optical purity of 99.56%, chemical purity of 99.83%, and a specific rotation of −149° (standard value of European Pharmacopoeia is −140°-152°). FIG. 9 and FIG. 10 are spectrograms showing chemical purity and optical purity of the product (S)-nicotine, respectively. In the figures, retention time for the chemical purity of (S)-nicotine was determined to be 19.239 min using a gas phase method, and retention time for the optical purity was determined to be 8.391 min using a liquid phase method.

Example 6

A method for synthesizing optically pure (S)-nicotine includes the following steps.

(1) 18.0 g of 4-hydroxy-1-(3-pyridyl)-1-butanone (0.11 mol, 1.0 eq) was dissolved in 4500 ml of potassium dihydrogen phosphate buffer with a concentration of 0.2 M (substrate concentration of 4 g/L); 0.08 g of PLP (0.33 mmol, 0.003 eq), 58.0 g of isopropylamine (0.98 mol, 9.0 eq), and 563.0 g of enzyme solution (transaminase A content of 16.0%) were added for the transamination reaction. The pH=8 was adjusted using 3.5% hydrochloric acid, the reaction temperature was 20-28° C., and the reaction time was 8 h. After completion of the reaction as determined by HPLC, the reaction solution was used directly in the next step.

(2) The above reaction solution (containing 16.3 g of (S)-4-amino-4-(3-pyridyl)-1-butanol (0.10 mol, 1.0 eq)) was cooled to 10° C.; and 13.0 g of dimethyl sulfate (0.10 mol, 1.05 eq) and 19.6 g of sodium hydroxide solution (containing NaOH 0.15 mol, 1.5 eq) at a concentration of 30% were added dropwise. After the addition dropwise, the temperature was at 0-5° C. for 6 h. After the completion of the reaction, the layers were separated, and the organic phase was dried using $Na_2SO_4$ to obtain a dichloromethane solution of (S)-4-(methylamino)-4-(3-pyridyl)-1-butanol.

(3) 17.3 g of diisopropylethylamine (0.13 mol, 1.5 eq) was added into the dichloromethane solution (containing 16.1 g of (S) -4-(methylamino)-4-(3-pyridyl) -1-butanol (0.09 mol, 1.0 eq)) obtained in step (2), and the temperature was cooled to −5° C. 17.0 g (0.09 mol, 1.0 eq) of p-toluenesulfonyl chloride was dissolved in 60 ml of dichloromethane to prepare a solution, and the temperature was controlled at <0° C. After slowly adding dropwise, the temperature was raised to 25° C. and maintained for 1.5 h. Upon completion of the central control reaction, a p-toluenesulfonate solution of (S)-4-(methylamino)-4-(3-pyridyl) butyl was obtained. The diisopropylethyl amine was used to adjust pH>8, and the temperature was raised to 50° C. for 2 h. After the completion of the central control ring closure reaction, 500 ml of aqueous solution was added, the aqueous phase was extracted once with 500 ml of dichloromethane, the organic phases were combined. $Na_2SO_4$ were added for drying, and the solvent was removed by concentration under reduced pressure to obtain crude (S)-nicotine. The crude (S)-nicotine was further purified by distillation to obtain 12.6 g of pure (S)-nicotine with a yield of 87.2% (total yield is 71.4% based on 4-hydroxy-1-(3-pyridyl)-1-butanone), optical purity of 99.5%, chemical purity of 99.7%, and a specific rotation of −149° (standard value of European Pharmacopoeia is −140°-152°).

The above are only preferred embodiments of the present disclosure and are not intended to limit the present disclosure. Although the present disclosure has been described in detail with reference to the aforementioned embodiments, it will be understood by those skilled in the art that the technical solutions recorded in the aforementioned embodiments may be modified, or some of the technical features may be equivalently replaced. Any modifications, equivalent substitutions, improvements, and the like made within the spirit and principles of the present disclosure shall be included within the scope of the present disclosure.

The invention claimed is:

1. A method for synthesizing a chiral intermediate (S)-4-amino-4-(3-pyridyl)-1-butanol for preparing (S)-nicotine, comprising:
performing a transamination reaction between 4-hydroxy-1-(3-pyridyl)-1-butanone and an amino donor to generate (S)-4-amino-4-(3-pyridyl)-1-butanol in catalysis of transaminase and coenzyme pyridoxal phosphate, the transaminase being one of transaminases with NCBI accession numbers being XP_007730450, 5FR9_A, WP_040602310 and XP_748821.

2. The method for synthesizing a chiral intermediate (S)-4-amino-4-(3-pyridyl)-1-butanol according to claim 1, wherein a temperature of the transamination reaction is 20-32° C., pH of the reaction is 6.5-8.0, and time for the reaction is 6-24 h.

3. The method for synthesizing a chiral intermediate (S)-4-amino-4-(3-pyridyl)-1-butanol according to claim 2, wherein the temperature of the transamination reaction is 28-30° C., the pH of the reaction is 7.0-8.0, and the time for the reaction is 8-12 h.

4. The method for synthesizing a chiral intermediate (S)-4-amino-4-(3-pyridyl)-1-butanol according to claim 1, wherein a mass ratio of 4-hydroxy-1-(3-pyridyl)-1-butanone and the transaminase is 1: 1-7.

5. The method for synthesizing a chiral intermediate (S)-4-amino-4-(3-pyridyl)-1-butanol according to claim 4, wherein the mass ratio of 4-hydroxy-1-(3-pyridyl)-1-butanone and the transaminase is 1: 3-7.

6. The method for synthesizing a chiral intermediate (S)-4-amino-4-(3-pyridyl)-1-butanol according to claim 1, wherein a molar ratio of 4-hydroxy-1-(3-pyridyl)-1-butanone and the amino donor is 1: 1-20; and the amino donor is one or more of isopropylamine, n-propylamine, alanine, and a-phenylethylamine.

7. The method for synthesizing a chiral intermediate (S)-4-amino-4-(3-pyridyl)-1-butanol according to claim 6, wherein the molar ratio of 4-hydroxy-1-(3-pyridyl)-1-butanone and the amino donor is 1: 9-10, and the amino donor is the isopropylamine.

8. A method for synthesizing a chiral intermediate (S)-4-(methylamino)-4-(3-pyridyl)-1-butanol for preparing (S)-nicotine, comprising:
preparing (S)-4-amino-4-(3-pyridyl)-1-butanol by the method according to claim 1; and performing an N-methylation reaction on (S)-4-amino-4-(3-pyridyl)-1-butanol with a methylating agent to obtain (S)-4-(methylamino)-4-(3-pyridyl)-1-butanol.

9. The method for synthesizing a chiral intermediate (S)-4-(methylamino)-4-(3-pyridyl)-1-butanol according to claim 8, wherein a temperature of the transamination reaction is 20-32° C., pH of the reaction is 6.5-8.0, and time for the reaction is 6-24 h.

10. The method for synthesizing a chiral intermediate (S)-4-(methylamino)-4-(3-pyridyl)-1-butanol according to claim 9, wherein in a method for synthesizing a chiral intermediate (S)-4-amino-4-(3-pyridyl)-1-butanol, the temperature of the transamination reaction is 28-30° C., the pH of the reaction is 7.0-8.0, and the time for the reaction is 8-12 h.

11. The method for synthesizing a chiral intermediate (S)-4-(methylamino)-4-(3-pyridyl)-1-butanol according to claim 8, wherein a mass ratio of 4-hydroxy-1-(3-pyridyl)-1-butanone and the transaminase is 1: 1-7.

12. The method for synthesizing a chiral intermediate (S)-4-(methylamino)-4-(3-pyridyl)-1-butanol according to claim 11, wherein the mass ratio of 4-hydroxy-1-(3-pyridyl)-1-butanone and the transaminase is 1: 3-7.

13. The method for synthesizing a chiral intermediate (S)-4-(methylamino)-4-(3-pyridyl)-1-butanol according to claim 8, wherein a molar ratio of 4-hydroxy-1-(3-pyridyl)-1-butanone and the amino donor is 1: 1-20; and the amino donor is one or more of isopropylamine, n-propylamine, alanine, and a-phenylethylamine.

14. The method for synthesizing a chiral intermediate (S)-4-(methylamino)-4-(3-pyridyl)-1-butanol according to claim 13, wherein the molar ratio of 4-hydroxy-1-(3-pyridyl)-1-butanone and the amino donor is 1: 9-10, and the amino donor is the isopropylamine.

15. The method for synthesizing a chiral intermediate (S)-4-(methylamino)-4-(3-pyridyl)-1-butanol according to claim 8, wherein the methylating agent is one or more of a combination of formic acid and formaldehyde, dimethyl sulfate, and methyl iodide.

16. The method for synthesizing a chiral intermediate (S)-4-(methylamino)-4-(3-pyridyl)-1-alcoholbutanol according to claim 8, wherein a molar ratio of (S)-4-amino-4-(3-pyridyl)-1-butanol and the methylating agent is 1: 1.05-1.3.

17. The method for synthesizing a chiral intermediate (S)-4-(methylamino)-4-(3-pyridyl)-1-butanol according to claim 16, wherein the molar ratio of (S)-4-amino-4-(3-pyridyl)-1-butanol and the methylating agent is 1: 1.05-1.1.

18. The method for synthesizing a chiral intermediate (S)-4-(methylamino)-4-(3-pyridyl)-1-butanol according to claim 8, wherein a temperature of the methylation reaction is 0-10° C.; and time for the reaction is 4-8 h.

19. The method for synthesizing a chiral intermediate (S)-4-(methylamino)-4-(3-pyridyl)-1-butanol according to claim 18, wherein the temperature of the reaction is 5-10° C.; and the time for the reaction is 4-6 h.

20. A method for synthesizing (S)-nicotine, comprising: preparing (S)-4-amino-4-(3-pyridyl)-1-butanol by the method according to claim 1; performing an N-methylation reaction on (S)-4-amino-4-(3-pyridyl)-1-butanol with a methylating agent to obtain (S)-4-(methylamino)-4-(3-pyridyl)-1-butanol, and making the obtained intermediate (S)-4-(methylamino)-4-(3-pyridyl)-1-butanol react with an acylating agent or a halogenating agent to convert an alcoholic hydroxyl group thereof into a sulfonate group or a halogen; and directly performing a ring closure reaction on a product without separation to obtain a final product (S)-nicotine with the reaction controlled in an alkaline condition.

* * * * *